United States Patent [19]
Le Coent et al.

[11] Patent Number: 6,162,770
[45] Date of Patent: Dec. 19, 2000

[54] UNSULFURIZED ALKALI METAL-FREE, ADDITIVE FOR LUBRICATING OILS

[75] Inventors: Jean-Louis Marie Le Coent, LeHavre; Jacques Cazin, Saint Martin du Manoir; Pierre Tequi, Saint-Romaint de Colbosc, all of France

[73] Assignee: Chevron Chemical Company LLC, San Francisco, Calif.

[21] Appl. No.: 09/236,979

[22] Filed: Jan. 26, 1999

[30] Foreign Application Priority Data

Jan. 30, 1998 [EP] European Pat. Off. .............. 98400203

[51] Int. Cl.⁷ .................................................. C10M 129/00
[52] U.S. Cl. ............................................. 508/460; 508/575
[58] Field of Search .................... 508/460, 575, 508/574

[56] References Cited

U.S. PATENT DOCUMENTS

| | | | |
|---|---|---|---|
| 3,036,971 | 5/1962 | Otto | 252/42.7 |
| 3,755,170 | 8/1973 | Rogers | 508/574 |
| 4,435,301 | 3/1984 | Brannen et al. | 508/392 |
| 5,330,665 | 7/1994 | Cane et al. | 508/394 |

FOREIGN PATENT DOCUMENTS

| | | | |
|---|---|---|---|
| 1 563 557 | 4/1969 | France . | |
| 2 625 220 | 6/1989 | France | C10M 159/22 |
| 95 00299 | 1/1995 | WIPO | B25J 19/00 |

*Primary Examiner*—Margaret Medley
*Assistant Examiner*—Cephia D. Toomer
*Attorney, Agent, or Firm*—Walter L. Stumpf; Richard J. Sheridan

[57] ABSTRACT

An unsulfurized, alkali metal-free, detergent-dispersant composition having from 40% to 60% alkylphenol, from 10% to 40% alkaline earth alkylphenate, and from 20% to 40% alkaline earth single aromatic-ring alkylsalicylate. This composition may have an alkaline earth double aromatic-ring alkylsalicylate as long as the mole ratio of single-ring alkylsalicylate to double aromatic-ring alkylsalicylate is at least 8:1. This composition may be produced by the three-step process involving neutralization of alkylphenols, carboxylation of the resulting alkylphenate, and filtration of the product of the carboxylation step.

4 Claims, No Drawings

UNSULFURIZED ALKALI METAL-FREE, ADDITIVE FOR LUBRICATING OILS

The present invention relates to an unsulfurized, alkali metal-free detergent-dispersant additive, comprising a mixture of alkaline earth metal salts (alkylphenate/ alkylsalicylate) and unreacted alkylphenols. This additive improves antioxidant properties, high temperature deposit control, and black sludge control.

BACKGROUND OF THE INVENTION

U.S. Pat. No. 3,036,971 discloses preparing detergent dispersant additives based on sulfurized alkylphenates of high basicity alkaline earth metals. These additives are prepared by sulfurization of an alkylphenol, neutralization of the sulfurized alkylphenol with an alkaline earth base, then super-alkalization by carbonation of the alkaline earth base dispersed in the sulfurized alkylphenate. French patent 1,563,557 discloses detergent additives based on sulfurized calcium alkylsalicylates. These additives are prepared by carboxylation of a potassium alkylphenate, exchange with calcium chloride, then sulfurization of the calcium alkylsalicylate obtained with sulfur in the presence of lime, a carboxylic acid and an alkylene glycol or alkyl ether of alkylene glycol.

Applicants' French patent application 2,625,220 discloses superalkalized detergent-dispersant additives based on alkylphenates and alkylsalicylates. These additives are prepared by neutralization of an alkylphenol with an alkaline earth base in the presence of an acid and a solvent, distillation of the solvent, carboxylation, sulfurization and superalkalization by sulfur and an alkaline earth base in the presence of glycol and solvent, followed by carbonation and filtration.

Applicants' PCT patent application PCT/FR95/00299 discloses a process that is able to improve substantially the performance of these additives, particularly in the tests relating to foaming, compatibility and dispersion in a new oil, and in the tests of stability towards hydrolysis. This process comprises neutralization with alkaline earth base of a mixture of linear and branched alkylphenols in the presence of a carboxylic acid, carboxylation by the action of carbon dioxide of the alkylphenate, followed by sulfurization and superalkalization, then carbonation, distillation, filtration, and degassing in air.

SUMMARY OF THE INVENTION

The present invention provides a method for producing an unsulfurized, alkali metal-free, additive for lubricating oils. That method comprises the neutralization of alkylphenols using an alkaline earth base in the presence of at least one carboxylic acid containing from one to four carbon atoms, in the absence of alkali base, in the absence of dialcohol, and in the absence of monoalcohol; followed by carboxylation of the alkylphenate produced in the neutralization step and filtration of the product of the carboxylation step.

This unsulfurized, alkali metal-free, additive can be obtained by filtration of an intermediate in the process described in PCT patent application PCT/FR95/00299. That intermediate is formed by neutralization with alkaline earth base of a mixture of linear and branched alkylphenols in the presence of a carboxylic acid and carboxylation by the action of carbon dioxide of the alkylphenate. We have discovered that the subsequent steps of sulfurization and superalkalization are not needed to make an additive having improved antioxidant properties, high temperature deposit control, and black sludge deposit control.

The alkylphenols contain up to 85% of linear alkylphenol in mixture with at least 15% of branched alkylphenol in which the branched alkyl radical contains at least nine carbon atoms. Preferably, the alkylphenols contain from 35% to 85% of linear alkylphenol in mixture with from 15% to 65% of branched alkylphenol. The ratio of branched versus linear alkylphenol is given by weight. Preferably, the linear alkyl radical contains 12 to 40 carbon atoms, more preferably from 18 to 30 carbon atoms, and the branched alkyl radical contains at least 9 carbon atoms, preferably from 9 to 24 carbon atoms, more preferably 10 to 15 carbon atoms, Preferably, alkaline earth base is selected from the group consisting of calcium oxide, calcium hydroxide, magnesium oxide, and mixtures thereof.

Preferably, the carboxylic acid is a mixture of formic acid and acetic acid, more preferably a 50/50 by weight mixture.

The neutralization operation is carried out at a temperature of at least 200° C., preferably at least 215° C. The pressure is reduced gradually below atmospheric in order to remove the water of reaction, in the absence of any solvent that may form an azeotrope with water. The quantities of reagents used correspond to the following molar ratios:

(1) alkaline earth base/alkylphenol of from 0.2:1 to 0.7:1, preferably from 0.3:1 to 0.5:1; and
(2) carboxylic acid/alkylphenol of from 0.01:1 to 0.5:1, preferably from 0.03:1 to 0.15:1.

In one embodiment, the neutralization step is carried out at a temperature of at least 240° C. with a gradual reduction in pressure below atmospheric so as to reach a pressure of no more than 7,000 Pa (70 mbars) at 240° C.

The alkylphenate obtained in the neutralization step is carboxylated in order to convert at least 20 mole % of the starting alkylphenols to alkylsalicylate using carbon dioxide under carboxylation conditions. Preferably, at least 22 mole % of the starting alkylphenols is converted, and this conversion occurs at a temperature between 180° C. and 240° C., under a pressure within the range of from above atmospheric pressure to $15 \times 10^5$ Pa (15 bars) for a period of one to eight hours.

Preferably, at least 25 mole % of the starting alkylphenols is converted to alkylsalicylate using carbon dioxide at a temperature equal to or greater than 200° C., under a pressure of $4 \times 10^5$ Pa (4 bars).

The product of the carboxylation step is then filtered to remove any sediment formed in the carboxylation step.

The detergent-dispersant produced by this method has the following composition:

(a) 40% to 60% alkylphenol,
(b) 10% to 40% alkaline earth alkylphenate, and
(c) 20% to 40% alkaline earth single aromatic-ring alkylsalicylate.

That detergent-dispersant composition may also comprise an alkaline earth double aromatic-ring alkylsalicylate, but the mole ratio of single aromatic-ring alkylsalicylate to double aromatic-ring alkylsalicylate will be at least 8:1.

That detergent-dispersant composition can be further characterized by the fact that the ratio of infrared transmittance band for aromatic ring out of plane C-H bending at about 763±3 cm$^{-1}$ to infrared transmittance band for aromatic ring out of plane C-H bending at about 832±3 cm$^{-1}$ is less than 0.1:1.

The detergent-dispersant produced by the method of the present invention can be used in an engine lubricating composition containing a major part of lubricating oil, from 1% to 30% of the detergent-dispersant, and preferably at least one other additive. Examples of other additives that can be included in the concentrate include alkaline earth metal detergents, ashless dispersants, oxidation inhibitors, rust inhibitors, demulsifiers, extreme pressure agents, friction modifiers, multifunctional additives, viscosity index improvers, pour point depressants, and foam inhibitors.

In marine applications, the black sludge deposit control, high temperature deposit control, and demulsibility performance of a lubricating oil can be improved by adding to the lubricating oil an effective amount of this detergent-dispersant.

In automotive applications, the high temperature deposit control performance and oxidation inhibition performance of a lubricating oil can be improved by adding to the lubricating oil an effective amount of the detergent-dispersant of the present invention.

The invention also provides a hydraulic oil composition with improved filterability containing a base oil of lubricating viscosity, from 0.1% to 3% of the detergent-dispersant of the present invention, and preferably at least one other additive.

The invention also provides a concentrate comprising the detergent-dispersant of the present invention, an organic diluent, and preferably at least one other additive. The organic diluent constitutes from 20% to 80% of the concentrate.

DETAILED DESCRIPTION OF THE INVENTION

Prior to discussing the invention in further detail, the following terms will be defined:

DEFINITIONS

As used herein, the following terms have the following meanings, unless expressly stated to the contrary:

The term "alkylphenol" means a phenol group having one or more alkyl substituents, at least one of which has a sufficient number of carbon atoms to impart oil solubility to the phenol.

The term "alkaline earth alkylphenate" means an alkaline earth metal salt of an alkylphenol.

The term "alkaline earth single aromatic-ring alkylsalicylate" means an alkaline earth metal salt of an alkyl salicylic acid, wherein there is only one alkyl salicylic anion per each alkaline earth metal base cation.

The term "alkaline earth double aromatic-ring alkylsalicylate" means an alkaline earth metal salt of an alkyl salicylic acid, wherein there are two alkyl salicylic anions per each alkaline earth metal base cation.

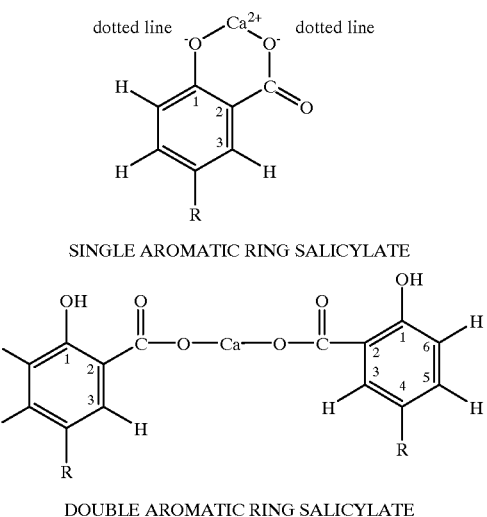

SINGLE AROMATIC RING SALICYLATE

DOUBLE AROMATIC RING SALICYLATE

The term "Base Number" or "BN" refers to the amount of base equivalent to milligrams of KOH in one gram of sample. Thus, higher BN numbers reflect more alkaline products, and therefore a greater alkalinity reserve. The BN of a sample can be determined by ASTM Test No. D2896 or any other equivalent procedure.

Unless otherwise specified, all percentages are in weight percent.

DETERGENT-DISPERSANT COMPOSITION

NEUTRALIZATION STEP

In the first step, alkylphenols are neutralized using an alkaline earth base in the presence of at least one $C_1$ to $C_4$ carboxylic acid. This reaction is carried out in the absence of alkali base, and in the absence of dialcohol or monoalcohol.

The alkylphenols contain up to 85% of linear alkylphenol (preferably at least 35% linear alkylphenol) in mixture with at least 15% of branched alkylphenol. Preferably, the linear alkyl radical contains 12 to 40 carbon atoms, more preferably 18 to 30 carbon atoms. The branched alkyl radical contains at least nine carbon atoms, preferably 9 to 24 carbon atoms, more preferably 10 to 15 carbon atoms.

The use of an alkylphenol containing at least 35% of long linear alkylphenol (from 18 to 30 carbon atoms) is particularly attractive because a long linear alkyl chain promotes the compatibility and solubility of the additives in lubricating oils. However, the presence of relatively heavy linear alkyl radicals in the alkylphenols makes the latter less reactive than branched alkylphenols, hence the need to use harsher reaction conditions to bring about their neutralization by an alkaline earth base.

Branched alkylphenols can be obtained by reaction of phenol with a branched olefin, generally originating from propylene. They consist of a mixture of monosubstituted isomers, the great majority of the substituents being in the para position, very few being in the ortho position, and hardly any in the meta position. That makes them relatively reactive towards an alkaline earth base, since the phenol function is practically devoid of steric hindrance.

On the other hand, linear alkylphenols can be obtained by reaction of phenol with a linear olefin, generally originating from ethylene. They consist of a mixture of monosubstituted isomers in which the proportion of linear alkyl substituents in the ortho, para, and meta positions is much more uniformly distributed. This makes them much less reactive towards an alkaline earth base since the phenol function is much less accessible due to considerable steric hindrance, due to the presence of closer and generally heavier alkyl substituents.

The alkaline earth bases that can be used for carrying out this step include the oxides or hydroxides of calcium, magnesium, barium, or strontium, and particularly of calcium oxide, calcium hydroxide, magnesium oxide, and mixtures thereof. In one embodiment, slaked lime (calcium hydroxide) is preferred.

The $C_1$ to $C_4$ carboxylic acids used in this step include formic, acetic, propionic and butyric acid, and may be used alone or in mixture. Preferably, a mixture of acids is used, most preferably a formic acid/acetic acid mixture. The molar ratio of formic acid/acetic acid should be from 0.2:1 to 100:1, preferably between 0.5:1 and 4:1, and most preferably 1:1. The carboxylic acids act as transfer agents, assisting the transfer of the alkaline earth bases from a mineral reagent to an organic reagent.

The neutralization operation is carried out at a temperature of at least 200° C., preferably at least 215° C., and more preferably at least 240° C. The pressure is reduced gradually below atmospheric in order to distill off the water of reaction. Accordingly the neutralization should be conducted in the absence of any solvent that may form an azeotrope with water. Preferably, the pressure is reduced to no more than 7,000 Pa (70 mbars).

The quantities of reagents used should correspond to the following molar ratios:

(1) alkaline earth base/alkylphenol of 0.2:1 to 0.7:1, preferably 0.3:1 to 0.5:1; and (2) carboxylic acid/alkylphenol of 0.01:1 to 0.5:1, preferably from 0.03:1 to 0.15:1.

Preferably, at the end of this neutralization step the alkylphenate obtained is kept for a period not exceeding fifteen hours at a temperature of at least 215° C. and at an absolute pressure of between 5,000 and $10^5$ Pa (between 0.05 and 1.0 bar). More preferably, at the end of this neutralization step the alkylphenate obtained is kept for between two and six hours at an absolute pressure of between 10,000 and 20,000 Pa (between 0.1 and 0.2 bar).

By providing that operations are carried out at a sufficiently high temperature and that the pressure in the reactor is reduced gradually below atmospheric, the neutralization reaction is carried out without the need to add a solvent that forms an azeotrope with the water formed during this reaction.

CARBOXYLATION STEP

The carboxylation step is conducted by simply bubbling carbon dioxide into the reaction medium originating from the preceding neutralization step and is continued until at least 20 mole % of the alkylphenate to alkylsalicylate (measured as salicylic acid by potentiometric determination). It must take place under pressure in order to avoid any decarboxylation of the alkylsalicylate that forms.

Preferably, at least 22 mole % of the starting alkylphenols is converted to alkylsalicylate using carbon dioxide at a temperature of between 180° and 240° C., under a pressure within the range of from above atmospheric pressure to $15\times10^5$ Pa (15 bars) for a period of one to eight hours.

According to one variant, at least 25 mole % of the starting alkylphenols is converted to alkylsalicylate using carbon dioxide at a temperature equal to or greater than 200° C. under a pressure of $4\times10^5$ Pa (4 bars).

FILTRATION STEP

The purpose of the filtration step is to remove sediments, and particularly crystalline calcium carbonate, which might have been formed during the preceding steps, and which may cause plugging of filters installed in lubricating oil circuits.

DETERGENT-DISPERSANT PRODUCT

The detergent-dispersant formed by this method can be characterize by its unique composition, with much more alkylphenol and alkaline earth single aromatic-ring alkylsalicylate than produced by other routes. That detergent-dispersant has the following composition;

(a) from 40% to 60% alkylphenol, (b) from 10% to 40% alkaline earth alkylphenate, and (c) from 20% to 40% alkaline earth single aromatic-ring alkylsalicylate.

Unlike alkaline earth alkylsalicylates produced by other process, this detergent-dispersant composition can be characterized by having only minor amounts of an alkaline earth double aromatic-ring alkylsalicylates. The mole ratio of single aromatic-ring alkylsalicylate to double aromatic-ring alkylsalicylate is at least 8:1.

Preferably, the BN of the detergent-dispersant should be from 100 to 150, more preferably from 110 to 130.

The detergent-dispersant formed by this method, being non-sulfurized, would provide improved high temperature deposit control performance over sulfurized products. Being alkali-metal free, this detergent-dispersant can be used in applications, such as marine engine oils, where the presence of alkali metals have proven to have harmful effects.

CHARACTERIZATION OF THE PRODUCT BY INFRARED SPECTROMETRY

Out-of-aromatic-ring-plane C-H bending vibrations were used to characterize the detergent-dispersant of the present invention.

Infrared spectra of aromatic rings show strong out-of-plane C-H bending transmittance band in the 675–870 $cm^{-1}$ region, the exact frequency depending upon the number and location of substituents. For ortho-disubstituted compounds, transmittance band occurs at 735–770 $cm^{-1}$. For para-disubstituted compounds, transmittance band occurs at 810–840 $cm^{-1}$.

Infrared spectra of reference chemical structures relevant to the present invention indicate that the out-of-plane C-H bending transmittance band occurs at 750±3 $cm^{-1}$ for ortho-alkylphenols, at 760±2 $cm^{-1}$ for salicylic acid, and at 832±3 $cm^{-1}$ for para-alkylphenols.

Alkaline earth alkylphenates known in the art have infrared out-of-plane C-H bending transmittance bands at 750±3 $cm^{-1}$ and at 832±3 $cm^{-1}$. Alkaline earth alkylsalicylates known in the art have infrared out-of-plane C-H bending transmittance bands at 763±3 cm$^{-1}$ and at 832±3 cm$^{-1}$.

The detergent-dispersant of the present invention shows essentially no out-of-plane C-H bending vibration at 763±3 cm$^{-1}$, even though there is other evidence that alkylsalicylate is present. This particular characteristic has not been fully explained. However, it may be hypothesized that the particular structure of the single aromatic ring alkylsalicylate prevents in some way this out-of-plane C-H bending vibration. In this structure, the carboxylic acid function is engaged in a cyclic structure, and thus may generate increased steric hindrance in the vicinity of the aromatic ring, limiting the free motion of the neighbor hydrogen atom. This hypothesis is supported by the fact that the infrared spectrum of the acidified product (in which the carboxylic acid function is no longer engaged in a cyclic structure and thus can rotate) has an out-of-plane C-H transmittance band at 763±3 cm$^{-1}$.

The detergent-dispersant of the present invention can thus be characterized by having a ratio of infrared transmittance band of out-of-plane C-H bending at about 763±3 cm$^{-1}$ to out-of-plane C-H bending at 832±3 cm$^{-1}$ of less than 0.1:1.

BASE OIL OF LUBRICATING VISCOSITY

The lubricating oil, or base oil, used in such compositions may be mineral oil or synthetic oils of viscosity suitable for use in the crankcase of an internal combustion engine, such as gasoline engines and diesel engines, which include marine engines. Lubricating oils have a viscosity of about 4 cSt to 32 cSt at 100° C. The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity, such as didodecyl benzene, can be used. Useful synthetic esters include the esters of monocarboxylic acids and polycarboxylic acids, as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acids and mono and dihydroxy alkanols can also be used.

Blends of mineral oils with synthetic oils are also useful. For example, blends of 10 to 25% hydrogenated 1-trimer with 75 to 90% 150 SUS (100° F.) mineral oil gives an excellent lubricating oil base.

OTHER ADDITIVE COMPONENTS

The following additive components are examples of some components that can be favorably employed in combination with the substituted hydrocarbaryl metal salt in the compositions of the present invention. These examples of additives are provided to illustrate the present invention, but they are not intended to limit it:

(1) Metal detergents: sulfurized or unsulfurized alkyl or alkenyl phenates, alkyl or alkenyl aromatic sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof.

(2) Ashless dispersants: alkenyl succinimides, alkenyl succinimides modified with other organic compounds, and alkenyl succinimides modified with boric acid, alkenyl succinic ester.

(3) Oxidation inhibitors
 (a) Phenol type oxidation inhibitors: 4,4'-methylene bis (2,6-di-tert-butylphenol), 4,4'-bis(2,6-di-tert-butylphenol), 4,4'-bis(2-methyl-6-tert-butylphenol), 2,2'-methylene bis (4-methyl-6-tert-butyl-phenol), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis (4-methyl-6-cyclohexylphenol), 2,6-di-tert-butyl-4-methyl-phenol, 2,6-di-tert-butyl4-ethylphenol, 2,4-dimethyl-6-tert-butyl-phenol, 2,6-di-tert-4-(N.N' dimethylaminomethylphenol), 4,4'-thiobis(2-methyl-6-tert-butylphenol), 2,2'-thiobis(4-methyl-6-tert-butylphenol), bis(3-methyl4-hydroxy-5-tert-butylbenzyl)-sulfide, and bis(3,5-di-tert-butyl-4-hydroxybenzyl).
 (b) Diphenylamine type oxidation inhibitor: alkylated diphenylamine, phenyl-α-naphthylamine, and alkylated α-naphthylamine.
 (c) Other types: metal dithiocarbamate (e.g., zinc dithiocarbamate), and methylenebis (dibutyl-dithiocarbamate).

(4) Rust inhibitors (Anti-rust agents)
 (a) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.
 (b) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(5) Demulsifiers: addition product of alkylphenol and ethyleneoxide, poloxyethylene alkyl ether, and polyoxyethylene sorbitan ester.

(6) Extreme pressure agents (EP agents): zinc dialkyldithiophosphate (primary alkyl type & secondary alkyl type), sulfurized oils, diphenyl sulfide, methyl trichlorostearate, chlorinated naphthalene, fluoroalkylpolysiloxane, and lead naphthenate.

(7) Friction modifiers: fatty alcohol, fatty acid, amine, borated ester, and other esters.

(8) Multifunctional additives: sulfurized oxymolybdenum dithiocarbamate, sulfurized oxymolybdenum organo phosphoro dithioate, oxymolybdenum monoglyceride, amine-molybdenum complex compound, and sulfur-containing molybdenym complex compound.

(9) Viscosity index improvers: polymethacrylate type polymers, ethylene-propylene copolymers, styrene-isoprene copolymers, hydrogenated styrene-isoprene copolymers, polyisobutylene, and dispersant type viscosity index improvers.

(10) Pour point depressants: polymethyl methacrylate.
(11) Foam Inhibitors: alkyl methacrylate polymers and dimethyl silicone polymers.

ENGINE LUBRICATING OIL COMPOSITION

The detergent-dispersant compositions produced by the process of this invention are useful for imparting detergency and dispersancy properties to a engine lubricating oil composition. When employed in this manner, the amount of the detergent-dispersant composition ranges from about 1% to 30% of the total lubricant composition, preferably from about 2% to 20% of the total lubricant composition. Such lubricating oil compositions are useful in automotive diesel and gasoline engines, as well as in marine engines. Such compositions are frequently used in combination with Group II metal detergents, and other additives.

Lubricating marine engines with an effective amount of lubricating oil having the detergent-dispersant of the present invention can control black sludge deposits. It also improves the high temperature deposit control performance and demulsibility performance of that lubricating oil in marine applications.

Adding an effective amount of the detergent-dispersant of the present invention to a lubricating oil improves the high temperature deposit control performance and the oxidation inhibition performance of that lubricating oil in automotive applications.

In one embodiment, an engine lubricating oil composition would contain (a) a major part of a base oil of lubricating viscosity;
(b) 1% to 20% of at least one ashless dispersant;
(c) 1% to 30% of the detergent/dispersant of the present invention;
(d) 0.05% to 5% of at least one zinc dithiophosphate;
(e) 0% to 10% of at least one oxidation inhibitor;
(f) 0% to 1% of at least one foam inhibitor; and
(g) 0% to 20% of at least one viscosity index improver.

In a further embodiment, an engine lubricating oil composition is produced by blending a mixture of the above components. The lubricating oil composition produced by that method might have a slightly different composition than the initial mixture, because the components may interact. The components can be blended in any order and can be blended as combinations of components.

HYDRAULIC OIL COMPOSITION

A hydraulic oil composition having improved filterability can be formed containing a major part of a base oil of lubricating viscosity, from 0.1% to 3% of the detergent-dispersant of the present invention, and preferably at least one other additive.

ADDITIVE CONCENTRATES

Additive concentrates are also included within the scope of this invention. The concentrates of this invention comprise the compounds or compound mixtures of the present invention, preferably with at least one other additive, as disclosed above. The concentrates contain sufficient organic diluent to make them easy to handle during shipping and storage.

From 20% to 80% of the concentrate is organic diluent. Suitable organic diluents which can be used include mineral oil or synthetic oils, as described above in the section entitled "Base Oil of Lubricating Viscosity."

EXAMPLES OF ADDITIVE PACKAGES

Below are representative examples of additive packages that can be used in a variety of applications. These representative examples employ the unsulfurized, alkali metal-free, additive of the present invention. That unsulfurized, alkali metal-free, additive may be used either with or without other metal-containing detergents, depending upon the desired BN of the final product. The following percentages are based on the amount of active component, with neither process oil nor diluent oil, but including sufficient metal-containing detergents (including other types of metal detergents) to achieve the desired BN. These examples are provided to illustrate the present invention, but they are not intended to limit it.

I. Marine Diesel Engine Oils

| | | |
|---|---|---|
| 1) | Detergent-dispersant additive | 65% |
| | Primary alkyl zinc dithiophosphate | 5% |
| | Oil of lubricating viscosity | 30% |
| 2) | Detergent-dispersant additive | 65% |
| | Alkenyl succinimide ashless dispersant | 5% |
| | Oil of lubricating viscosity | 30% |
| 3) | Detergent-dispersant additive | 60% |
| | Primary alkyl zinc dithiophosphate | 5% |
| | Alkenyl succinimide ashless dispersant | 5% |
| | Oil of lubricating viscosity | 30% |
| 4) | Detergent-dispersant additive | 65% |
| | Phenol type oxidation inhibitor | 10% |
| | Oil of lubricating viscosity | 25% |
| 5) | Detergent-dispersant additive | 55% |
| | Alkylated diphenylamine-type oxidation inhibitor | 15% |
| | Oil of lubricating viscosity | 30% |
| 6) | Detergent-dispersant additive | 65% |
| | Phenol-type oxidation inhibitor | 5% |
| | Alkylated diphenylamine-type oxidation inhibitor | 5% |
| | Oil of lubricating viscosity | 25% |
| 7) | Detergent-dispersant additive | 60% |
| | Primary alkyl zinc dithiophosphate | 5% |
| | Phenol-type oxidation inhibitor | 5% |
| | Oil of lubricating viscosity | 30% |
| 8) | Detergent-dispersant additive | 60% |
| | Alkenyl succinimide ashless dispersant | 5% |
| | Alkylated diphenylamine-type oxidation inhibitor | 10% |
| | Oil of lubricating viscosity | 25% |
| 9) | Detergent-dispersant additive | 55% |
| | Other additives | 25% |
| | Primary alkyl zinc dithiophosphate | |
| | Alkenyl succinic ester ashless dispersant | |
| | Phenol-type oxidation inhibitor | |
| | Alkylated diphenylamine-type oxidation inhibitor | |
| | Oil of lubricating viscosity | 30% |

II. Motor Car Engine Oils

| | | |
|---|---|---|
| 1) | Detergent-dispersant additive | 25% |
| | Alkenyl succinimide ashless dispersant | 35% |
| | Primary alkyl zinc dithiophosphate | 10% |
| | Oil of lubricating viscosity | 30% |
| 2) | Detergent-dispersant additive | 20% |
| | Alkenyl succinimide ashless dispersant | 40% |
| | Secondary alkyl zinc dithiophosphate | 5% |
| | Dithiocarbamate type oxidation inhibitor | 5% |
| | Oil of lubricating viscosity | 30% |

-continued

| | | |
|---|---|---|
| 3) | Detergent-dispersant additive | 20% |
| | Alkenyl succinimide ashless dispersant | 35% |
| | Secondary alkyl zinc dithiophosphate | 5% |
| | Phenol type oxidation inhibitor | 5% |
| | Oil of lubricating viscosity | 35% |
| 4) | Detergent-dispersant additive | 20% |
| | Alkenyl succinimide ashless dispersant | 30% |
| | Secondary alkyl zinc dithiophosphate | 5% |
| | Dithiocarbamate type anti-wear agent | 5% |
| | Oil of lubricating viscosity | 40% |
| 5) | Detergent-dispersant additive | 20% |
| | Succinimide ashless dispersant | 30% |
| | Secondary alkyl zinc dithiophosphate | 5% |
| | Molybdenum-containing anti-wear agent | 5% |
| | Oil of lubricating viscosity | 40% |
| 6) | Detergent-dispersant additive | 20% |
| | Alkenyl succinimide ashless dispersant | 30% |
| | Other additives | 10% |
| | Primary alkyl zinc dithiophosphate | |
| | Secondary alkyl zinc dithiophosphate | |
| | Alkylated diphenylamine-type oxidation inhibitor | |
| | Dithiocarbamate type anti-wear agent | |
| | Oil of lubricating viscosity | 40% |
| 7) | Detergent-dispersant additive | 60% |
| | Other additives | |
| | Phenol type oxidation inhibitor | |
| | Alkylated diphenylamine-type | |
| | Oxidation inhibitor | |
| | Dithiocarbamate type anti-wear agent | |
| | Demulsifier | |
| | Boron-containing friction modifier | |
| | Oil of lubricating viscosity | 30% |

III. Hydraulic Oils

| | | |
|---|---|---|
| 1) | Detergent-dispersant additive | 20% |
| | Primary alkyl zinc dithiophosphate | 50% |
| | Other additives | 25% |
| | Phenol type oxidation inhibitor | |
| | Phosphorous-containing extreme pressure agent | |
| | Triazol type corrosion inhibitor | |
| | Demulsifier | |
| | Nonionic anti-rust agent | |
| | Oil of lubricating viscosity | 5% |
| 2) | Detergent-dispersant additive | 10% |
| | Primary alkyl zinc dithiophosphate | 40% |
| | Other additives | |
| | Phenol type oxidation inhibitor | |
| | Sulfur-containing extreme pressure agent | |
| | Triazol type corrosion inhibitor | |
| | Demulsifier | |
| | Nonionic anti-rust agent | |
| | Oil of lubricating viscosity | 3% |
| 3) | Detergent-dispersant additive | 10% |
| | Phosphorous-containing extreme pressure agent | 40% |
| | Phenol type oxidation inhibitor | 15% |
| | Other additives | 25% |
| | Diphenylamine type oxidation inhibitor | |
| | Sulfur-containing extreme pressure agent | |
| | Triazol type corrosion inhibitor | |
| | Demulsifier | |
| | Nonionic anti-rust agent | |
| | Oil of lubricating viscosity | 10% |
| 4) | Detergent-dispersant additive | 20% |
| | Phosphorous-containing extreme pressure agent | 30% |
| | Other additives | 45% |
| | Diphenylamine type oxidation inhibitor | |
| | Sulfur-containing extreme pressure agent | |
| | Triazol type corrosion inhibitor | |
| | Demulsifier | |
| | Nonionic anti-rust agent | |
| | Oil of lubricating viscosity | 5% |

IV. Transmission Hydraulic Fluids

| | | |
|---|---|---|
| 1) | Detergent-dispersant additive | 35% |
| | Primary alkyl zinc dithiophosphate | 20% |
| | Polyol type friction modifier | 20% |
| | sulfur-containing extreme pressure agent | 5% |
| | Oil of lubricating viscosity | 20% |
| 2) | Detergent-dispersant additive | 40% |
| | Primary alkyl zinc dithiophosphate | 15% |
| | Amide type friction modifier | 15% |
| | Sulfur-containing extreme pressure agent | 5% |
| | Oil of lubricating viscosity | 25% |
| 3) | Detergent-dispersant additive | 30% |
| | Primary alkyl zinc dithiophosphate | 20% |
| | Other additives | 30% |
| | Alkenyl succinimide ashless dispersant | |
| | Amide type friction modifier | |
| | Ester type friction modifier | |
| | Phosphorous, Sulfur-containing extreme pressure agent | |
| | Oil of lubricating viscosity | 20% |
| 4) | Detergent-dispersant additive | 35% |
| | Primary alkyl zinc dithiophosphate | 15% |
| | Other additives | |
| | Polyol type friction modifier | |
| | Amide type friction modifier | |
| | Phosphorous, Sulfur-containing extreme pressure agent | |
| | Oil of lubricating viscosity | 25% |

EXAMPLES

The invention will be further illustrated by following examples, which set forth particularly advantageous method embodiments. While the Examples are provided to illustrate the present invention, they are not intended to limit it.

PREPARATION OF NOVEL DETERGENT-DISPERSANT ADDITIVE

Example 1

A. Neutralization:

A charge of 875 g of branched dodecylphenol (DDP) having a molecular mass of 270, (i.e. 3.24 moles) and 875 g of linear alkylphenol having a molecular mass of about 390 (i.e. 2.24 moles) was placed in a four-necked 4 liter glass reactor above which was a heat-insulated Vigreux fractionating column. The isomeric molar repartition of para versus ortho alkylphenol was:

DDP: 89% para and 5.5% ortho Linear alkylphenol: 39% para and 53% ortho.

The agitator was started up and the reaction mixture was heated to 65° C., at which temperature 158 grams of slaked lime $Ca(OH)_2$ (i.e. 2.135 moles) and 19 g of a mixture (50/50 by weight) of formic acid and acetic acid were added.

The reaction medium underwent further heating to 120° C. at which temperature the reactor was placed under a nitrogen atmosphere, then heated up to 165° C. and then the nitrogen introduction was stopped. Distillation of water commenced at this temperature.

The temperature was increased to 240° C. and the pressure was reduced gradually below atmospheric until an absolute pressure of 5,000 Pa (50 mbars) was obtained.

The reaction mixture was kept for five hours under the preceding conditions. The reaction mixture was allowed to cool to 180° C., then the vacuum was broken under a nitrogen atmosphere and a sample was taken for analysis. The total quantity of distillate obtained was about 120 cm$^3$; demixing took place in the lower phase (66 cm$^3$ being water).

B. Carboxylation:

The product obtained in Step (A) was transferred to a 3.6-liter autoclave and heated to 180° C.

At this temperature, scavenging of the reactor with carbon dioxide ($CO_2$) was commenced and continued for ten minutes. The amount of $CO_2$ used in this step was in the order of 20 grams.

After the temperature had been raised to 200° C., the autoclave was closed, leaving a very small leak, and the introduction of $CO_2$ was continued so as to maintain a pressure of $3.5 \times 10^5$ Pa (3.5 bars) for 5 hours at 200° C. The amount of $CO_2$ introduced was in the order of 50 grams. After the autoclave had been cooled to 165° C., the pressure was restored to atmospheric and the reactor was then purged with nitrogen.

A total quantity of 1,912 grams of product was recovered prior to filtration. The product was then filtered.

C. Analytical characterization

The following analytical protocol was used to characterize the detergent-dispersants of the present invention.

Neat Component Base Number (BN) % Calcium (% Ca) Salicylic acid index (SAI)

Dialysis of Neat Component Dialysate % Weight (%) % Calcium (% Ca)

Residue % Weight (%) % Calcium (% Ca) % Conversion to Salicylic acid (% SA)

Dialysis was performed for six hours on an 8 to 9 grams sample through a rubber membrane, using pentane at reflux as a solvent.

% Ca was determined by classical X Ray spectrometry.

SAI is a measure of the quantity of alkylsalicylate formed in the detergent-dispersant. It was determined by acidification of the product by a strong acid (hydrochloric acid) in the presence of diethyl ether, followed by a potentiometric titration on the organic fraction (tetra n-butyl ammonium hydroxide was used as a titration agent). Results were expressed in equivalent mg KOH per gram of product (Base Number unit).

% SA was determined on the dialysis residue by acidification of the product by a strong acid (hydrochloric acid) in the presence of diethyl ether, followed by a potentiometric titration on the organic fraction (tetra n-butyl ammonium hydroxide was used as a titration agent). This method separates and quantifies the alkyl salicylic acid and the remaining alkylphenol (non-carboxylated alkylphenate). Results were expressed in equivalent mg KOH per gram of product (Base Number unit). % SA was then determined by using the following equation:

% SA=100 * (Alkylsalicylic acid/ (Alkylphenol+ Alkylsalicylic acid))

Analytical results on EXAMPLE 1

Neat Component Base Number of 118 4.2% Calcium Salicylic acid index of 49

Dialysis of Neat Component Dialysate 53% Weight 0% Calcium

Residue 47% Weight 8.8% Calcium 74% Conversion to Salicylic acid

Comparison of Measured % Calcium on residue with calculated values based on Hypothesized Alkylsalicylate structures

| Name of Product | Average Mw | Average % Ca |
|---|---|---|
| Alkylphenol mixture | 319 | |
| Calcium Alkylphenate | 676 | 5.9% |
| Single Aromatic ring Alkylsalicylate | 401 | 10.0% |
| Double Aromatic ring Alkylsalicylate | 764 | 5.2% |

The following equation leads to the theoretical % Ca for the residue

% Ca=(% SA * % Ca Alkylsalicylate)+((100− % SA) * % Ca Alkylphenate)

If the Alkylsalicylate is in the Single aromatic ring structure the theoretical % Ca (residue) is 8.9%

If Alkylsalicylate is in the Double aromatic ring structure the theoretical % Ca (residue) is 5.4%.

The result of 8.7% is well in agreement with the measured % Ca in the residue (8.8%), showing that the structure of the alkylsalicylate moiety is essentially the single aromatic ring structure.

Based on the above data, the composition of the Neat component is: 34.8% Alkylsalicylate (essentially in the single aromatic ring structure) 12.2% Alkylphenate. 53% Unreacted Alkylphenol Example 2

Batch procedure and loads of Example I were reproduced except for the quantity of formic and acetic acids (16.4 grams total instead of 19 grams).

Example 3

Batch procedure and loads of Example I were reproduced except for the temperature of neutralization (which was lower, 220° C. instead of 240° C.) and the quantity of lime, which was lower (CMR lime/alkylphenols being 0.34 instead of 0.39).

Examples 4 and 5

Batch procedure and loads of Example III were reproduced except that the weight ratio of branched alkylphenol to linear alkylphenol was 40/60 in Example IV and was 60/40 in Example V, compared to 50/50 in Example I.

| Charges (g) | 1 | 2 | 3 | 4 | 5 |
|---|---|---|---|---|---|
| A. Neutralization | | | | | |
| Dodecylphenol (branched) | 875 | 875 | 875 | 700 | 1050 |
| Alkylphenol (linear) | 875 | 875 | 875 | 1050 | 700 |
| Lime | 158 | 158 | 137.7 | 137.7 | 137.7 |
| Formic acid | 9.5 | 8.2 | 9.5 | 8.2 | 8.2 |
| Acetic acid | 9.5 | 8.2 | 9.5 | 8.2 | 8.2 |
| CMR | | | | | |
| Lime/Alkylphenol | 0.39 | 0.39 | 0.34 | 0.35 | 0.328 |
| (Formica + Acetidc)/ Alkylphenol | 0.066 | 0.057 | 0.066 | 0.059 | 0.055 |
| B. Analysis | | | | | |
| Before filtration BN (ASTM D 2896) | 125 | 120 | 105 | 94 | 110 |
| After filtration | 118 | 113 | 98 | 89 | 105 |

-continued

| Charges (g) | 1 | 2 | 3 | 4 | 5 |
|---|---|---|---|---|---|
| BN (ASTM D 2896) | | | | | |
| % Ca - X ray | 4.21 | 4.03 | 3.5 | 3.18 | 3.75 |
| vol % SED ASTM D 2273 | 0.01 | 0.01 | 0.01 | 0.01 | 0.01 |
| Salicylic index, mg HOH/g (ASTM D 2896) | 49 | 46.9 | 40.7 | 33 | 42 |
| Conversion | 32 | 30.6 | 26 | 22 | 30 |

PROCEDURES FOR PERFORMANCE TESTS

The following Section describes Performance Test Methods referred to in these examples.

Demulsibility (ASTM D1401)

This test evaluates the ability of oils to separate from water, without forming stable emulsions. In this test, an oil sample and distilled water are stirred in a graduated cylinder. The volume of remaining emulsion after one hour is reported.

High Temperature Cleanliness Test (H.T.C.T.)

This test evaluates the detergent power of a lubricant in marine engines burning heavy fuel (HFO). A lubricant sample is contaminated with heavy fuel without stirring. The glassware containing the mixture lubricant/HFO is heated at 175° C. and oxidized by air for 48 hours. After cooling, the glassware is drained in a beaker. Deposits formed on the inner wall of the glassware are rated according to the following demerit scale 1. Clean
2. Slightly Dirty
3. Moderately Dirty
4. Dirty
5. Very Dirty Hot Tube Test (H.T.T.)

This test evaluates the detergency power of a lubricant at high temperature and its thermal stability, by rating the lacquers formed on glass test tubes. A glass tube in which the oil sample circulates under an air flow is put into a furnace heated at high temperature. The lacquer appearing on the walls of glass tubes are rated by comparison to a reference lacquer color chart (10=clean, 0=black).

Black Sludge Control Test (B.S.C.T.)

This test evaluates the ability of a lubricant to control black sludge deposit formation in marine engines burning heavy fuel (HFO). Some sludge (soot particles) and HFO are introduced in the lubricant (with or without water). After stirring, a drop of contaminated lubricant is settled on a sheet of filter paper after different thermal treatments. The same procedure is applied after pre-aging of the oil. The black sludge control performance is calculated by measuring the spots ratio after 48 hour spot expansion at room temperature. The higher the number, the better the black sludge deposit control performance.

Microcoking Test (M.C.T.)

This test evaluates the tendency of a lubricant to form deposit at high temperature, and its detergent power. A pre-aged oil sample is heated on an aluminum test plate, to which a temperature gradient is applied. The temperature at which deposit first appear is reported. The higher the temperature, the better performance.

Panel Coker Test (P.C.T)

This test evaluates the tendency of the lubricant to form carbon deposits when in contact with metallic surfaces at high temperature. An oil sample is preheated in a sump and then intermittently projected (by the mean of a rotating oil stirrer) on an aluminum test plate heated at high temperature. The amount of deposit is weighed at the end of test. The lower the number, the better the result.

DSC Oxidation Test (DSC)

This test method evaluates the oxidative stability of lubricants under thin film condition. An oil sample (2–3 mg) is put in an aluminum crucible with an oxidation catalyst. This crucible is placed in an oven on a sensor which measures the difference between the heat flow of the lubricant and the heat flow of an empty reference crucible. A controlled stream of oxygen circulates in the oven. Oxidation induction time is detected by a sharp increase of the heat flow. Oxidation induction time is reported. The longer the time, the better the oxidative stability of the lubricant.

Filterability AFNOR NFE 48690

This test evaluates the filterability of hydraulic oil. A sample of oil is filtered through a membrane of cellulose ester (0.8 µ) and the Filterability Index (IFE) is determined by the following equation:

$$IFE \frac{\text{time to filter 300 ml} - \text{time to filter 200 ml}}{2 * (\text{time to filter 100 ml} - \text{time to filter 50 ml})}$$

The closer the IFE to 1, the better the filterability

Filterability AFNOR NFE 48691

This test evaluates the filterability of hydraulic oil in the presence of water as a contaminant. A sample of oil is filtered through a membrane of cellulose ester (0.8 µ) and the Filterability Index (IFE) is determined.

$$IFE \frac{(\text{time to filter 300 ml} - \text{time to filter 200 ml})}{2 * (\text{time to filter 100 ml} - \text{time to filter 50 ml})}$$

The closer the IFE to 1, the better the filterability

EXAMPLES SHOWING PERFORMANCE ADVANTAGES

The following Examples illustrate performance advantages claimed in the present invention.

Example 6 Marine Engine Oils Performance

The additive concentrates used in the present example were generated for lubricants intended for use in Marine Trunk Piston Engines and had the following compositions:

| Formula 1 | |
|---|---|
| Succinimide | 8% |
| Zinc Alkyl Dithiophosphate | 3.5% |
| Commercial detergent/dispersant | 75% |
| Formula 2 | |
| Succinimide | 8% |
| Zinc Alkyl Dithiophosphate | 3.5% |
| Example I | 35% |
| HOB sulfonate | 40% |

-continued

| Formula 3 | |
|---|---|
| Succinimide | 8% |
| Zinc Alkyl Dithiophosphate | 3.5% |
| HOB sulfonate | 75% |

The treat rates of these concentrated additives in finished oil were adjusted to ensure a BN of 40 mg KOH/g according to ASTM D2896 for the finished lubricant.

| Formula | 1 | 2 | 3 |
|---|---|---|---|
| ASTM D1401 (water separated after 1 hour) | 0 cc | 24 cc | |
| HTCT Demerit | 3 | 2 | 5 |
| HTT Merit | 3.5 | 6 | 0 |
| BSCT (Rating/600) | 388 | 395 | 0 |
| MCT temperature of deposit | 245° C. | 250° C. | <230° C. |

Example 7 Automotive Performance

The additive concentrates used in the present example were designed for lubricants intended for use in Super-High Performance Diesel Oil (SHPDO) and had the following compositions:

| Formula 4 | |
|---|---|
| Succinimide | 45% |
| Zinc Alkyl dithiophosphate | 12% |
| Oxidation inhibitor | 4% |
| Commercial detergent | 33% |

| Formula 5 | |
|---|---|
| Succinimide | 45% |
| Zinc Alkyl dithiophpsphate | 12% |
| Oxidation inhibitor | 4% |
| Example I | 39% |

The following table also includes performance data of an SHPDO high performance reference oil (RL1 96/1) for comparison purposes.

| Formula | 4 | 5 | RL 196/1 |
|---|---|---|---|
| Panel Coker weight deposit | 600 mg | 2 mg | 700 mg |
| Hot Tube Test merit | 4.5 | 10 | 2.5 |
| DSC Induction time (minutes) | 55 | 140 | 100 |

Example 8 Hydraulic Oils

The additive concentrates used in the present example were designed for lubricants intended for use in Hydraulic oils (DENISON HFO)

| Formula 6 | |
|---|---|
| Wear inhibitor | 44.4% |
| Filterability improving agent | 5.6% |
| Oxidation inhibitor | 22.2% |
| Commercial detergent | 8.8% |

| Formula 7 | |
|---|---|
| Wear inhibitor | 44.4% |
| Filterability improving agent | 5.6% |
| Oxidation inhibitor | 22.2% |
| Commercial detergent | 8.8% |
| Example I | 6.6% |

The treat rates of these concentrates in the finished oil were 0.9%.

| Formula | 6 | 7 |
|---|---|---|
| AFNOR NFE 48690 Filterability Index | 1.24 | 1.16 |
| AFNOR NFE 48691 Filterability Index | 1.13 | 1 |

While the present invention has been described with reference to specific embodiments, this application is intended to cover those various changes and substitutions that may be made by those skilled in the art without departing from the spirit and scope of the appended claims.

What is claimed is:

1. A method for producing an unsulfurized, alkali metal-free additive for lubricating oils comprising:
   (a) neutralizing alkylphenols using an alkaline earth base in the presence of at least one carboxylic acid containing from one to four carbon atoms, and in the absence of alkali base, dialcohol, and monoalcohol, to produce an alkylphenate wherein:
   (1) said neutralizing operation is carried out at a temperature of at least 200° C.;
   (2) the neutralizing operation is carried out at a pressure that is reduced gradually below atmospheric in order to remove the water of reaction, in the absence of any solvent that may form an azeotrope with water;
   (3) said alkylphenols contain up to 85% of linear alkylphenol in mixture with at least 15% of branched alkylphenol in which the branched alkyl radical contains at least nine carbon atoms; and
   (4) the quantities of reagents used correspond to the following molar ratios:
   (a) alkaline earth base/alkylphenol of 0.2:1 to 0.7:1;
   (b) carboxylic acid/alkylphenol of from 0.01:1 to 0.5:1;
   (b) carboxylating the alkylphenate obtained in step (a) using carbon dioxide under carboxylation conditions sufficient to convert at least 20 mole % of the starting alkylphenols to alkylsalicylate; and
   (c) filtering the product produced in step (b) to remove any sediment.

2. A method for producing an unsulfurized, alkali metal-free additive for lubricating oils according to claim 1, wherein, (a) in said neutralizing step:
  (1) said neutralizing is carried out at a temperature of at least 215° C.;
  (2) said alkylphenols contain from 35% to 85% of linear alkylphenol in mixture with from 15% to 65% of branched alkylphenol,
    (a) in which the linear alkyl radical contains from 18 to 30 carbon atoms, and
    (b) in which the branched alkyl radical contains an average of from 10 to 15 carbon atoms;
  (3) said alkaline earth base is selected from the group consisting of calcium oxide, calcium hydroxide, magnesium oxide, and mixtures thereof;
  (4) said carboxylic acid is a mixture of formic acid and acetic acid; and
  (5) said quantities of reagents used correspond to the following molar ratios:
    (a) alkaline earth base/alkylphenol of 0.3:1 to 0.5:1, and
    (b) carboxylic acid/alkylphenol of 0.03:1 to 0.15:1; and
(b) in said carboxylating step,
  (1) at least 22 mole % of the starting alkylphenols is converted to alkylsalicylate, and
  (2) a temperature of between 180° C. and 240° C., a pressure of from above atmospheric pressure to $15 \times 10^5$ Pa (15 bars), and a period of time from one to eight hours is used.

3. A method for producing an unsulfurized, alkali metal-free, additive for lubricating oils according to claim 2, wherein,
(a) in said neutralizing step:
  (1) said neutralizing is carried out at a temperature of at least 240° C.;
  (2) said carboxylic acid is a 50/50 by weight mixture of formic acid and acetic acid; and
  (3) said gradual reduction in pressure reaches a pressure of no more than 7,000 Pa (70 mbars) at 240° C.; and
(b) in said carboxylating step,
  (1) at least 25 mole % of the starting alkylphenols is converted to alkylsalicylate, and
  (2) the temperature is at least 200° C., and the pressure is $4 \times 10^5$ Pa (4 bars).

4. A detergent-dispersant produced by the method according to claim 1.

* * * * *